United States Patent [19]

Bazzano

[11] Patent Number: 5,514,672
[45] Date of Patent: May 7, 1996

[54] USE OF RETINOIDS AND COMPOSITIONS CONTAINING SAME FOR HAIR GROWTH

[76] Inventor: Gail S. Bazzano, 4506 Avron Blvd., Metairie, La. 70006

[21] Appl. No.: 283,649

[22] Filed: Dec. 13, 1988

Related U.S. Application Data

[63] Continuation-in-part of Ser. No. 136,525, Dec. 22, 1987, abandoned, which is a continuation of Ser. No. 463,146, Feb. 2, 1983, abandoned, which is a continuation-in-part of Ser. No. 235,169, Feb. 17, 1981, abandoned, Ser. No. 318,607, Nov. 9, 1981, abandoned, Ser. No. 386,730, Jun. 9, 1982, abandoned, and Ser. No. 414,854, Sep. 3, 1992, abandoned.

[51] Int. Cl.$^6$ .................................................. A61K 7/06
[52] U.S. Cl. .................... 514/168; 424/70.1; 514/725; 514/880; 514/881; 514/946
[58] Field of Search .................................... 514/725, 880, 514/881, 168, 946; 8/94.14

[56] References Cited

U.S. PATENT DOCUMENTS

| | | | |
|---|---|---|---|
| 2,268,736 | 11/1942 | Buxton et al. | 514/168 |
| 2,276,531 | 3/1942 | Wechsler et al. | 514/168 |
| 2,310,479 | 2/1943 | Vollmer | 514/946 |
| 2,865,859 | 12/1958 | Lubowe | 514/847 |
| 3,382,248 | 5/1968 | Anthony et al. | 424/70 |
| 3,461,461 | 8/1969 | Anthony et al. | 424/70 |
| 3,464,987 | 9/1969 | Ursprung | 424/70 |
| 3,711,606 | 1/1973 | Herschler | 514/946 |
| 3,729,568 | 4/1973 | Kligman . | |
| 3,882,244 | 5/1975 | Lee | 424/70 U X |
| 3,973,016 | 8/1976 | Morrison | 424/70 |
| 3,991,203 | 11/1976 | Rajadhydaksha | 514/946 |
| 4,034,114 | 7/1977 | Yu et al. | 514/168 |
| 4,139,619 | 12/1979 | Chielsey | 514/725 U X |
| 4,170,229 | 10/1979 | Olson | 424/70 U X |
| 4,201,235 | 5/1980 | Cianatta | 514/168 |
| 4,220,772 | 9/1980 | Muller et al. | 424/70 |
| 4,247,547 | 1/1981 | Marks | 424/70 U X |
| 4,287,338 | 9/1981 | McCall | 424/70 |
| 4,304,787 | 12/1981 | Gander et al. | 424/70 U X |
| 4,322,438 | 3/1982 | Peck | 424/70 U X |
| 4,333,924 | 6/1982 | Bowler et al. | 424/70 U X |
| 4,985,464 | 1/1991 | Happle et al. | 514/880 |

FOREIGN PATENT DOCUMENTS

| | | | |
|---|---|---|---|
| 158799 | 9/1954 | Australia | 424/70 U X |
| 553262 | 12/1956 | Belgium | 424/70 U X |
| 024967 | 3/1987 | European Pat. Off. | 424/70 |
| 2758485 | 5/1980 | Germany | 424/70 |
| 906000 | 9/1962 | United Kingdom | 424/70 |
| 1466062 | 3/1977 | United Kingdom | 424/70 |
| 1487543 | 5/1977 | United Kingdom | 424/70 |

OTHER PUBLICATIONS

Conn, Current Therapy, 1981, p. 662.
Conn, Current Therapy, 1984, pp. 599 to 603.
9007/80, Jan. 1980, Japan laid open publication (translated claims).
73137/76, Jun. 1976, Japan laid open publication (translated claim and summary).
Saitoh, M. et al. "Rate of Hair Growth" Chapter XIV, pp. 183–201.
Pinkus, H. "Alternations of the Hair Follicle in Hair Diseases," pp. 237–243 in *Hair Research* Orafanos et al. (ed.) Springer–Verlang 1981.

*Primary Examiner*—Shelley A. Dodson
*Attorney, Agent, or Firm*—Panitch Schwarze Jacobs & Nadel

[57] ABSTRACT

Increase in the rate of hair growth, stimulation of hair follicles to produce new hair growth, prolongation of the anagen phase of the hair cycle, and conversion of vellus hair to growth as terminal hair, and treatment of alopecias due to organic dysfunction of the hair follicle is attained in mammalian skins by either oral administration or by topical application to the skin, hair and/or hair follicles of the mammal of effective amounts of a retinoid, particularly retinoic acid. The retinoid may be administered or applied alone or with other adjunctive compounds including vitamins, such as Vitamin $D_3$, hormones, antiandrogens and/or vasodilators.

36 Claims, No Drawings

# USE OF RETINOIDS AND COMPOSITIONS CONTAINING SAME FOR HAIR GROWTH

CROSS-REFERENCE TO RELATED APPLICATIONS

This application is a continuation-in-part of application Ser. No. 136,525, filed Dec. 22, 1987, now abandoned which in turn is a continuation of Ser. No. 463,146, filed Feb. 2, 1983, now abandoned, which in turn is a continuation-in-part of applications Ser. No. 235,169, filed Feb. 17, 1981; Ser. No. 318,607, filed Nov. 9, 1981; Ser. No. 386,730, filed Jun. 9, 1982; and Ser. No. 414,854, filed Sep. 3, 1982, all now abandoned. This application is also related to my co-pending application Ser. No. 283,646, filed concurrently herewith, entitled "Combinations of Retinoids and Minoxidil-Type Compounds For Hair Growth".

FIELD OF INVENTION

This invention generally relates to hair growth and, more particularly, it relates to compositions and methods for increasing the rate of and stimulating hair growth on mammalian skins, prolonging the anagen phase of the hair cycle, and converting vellus hair to growth as terminal hair.

BACKGROUND OF THE INVENTION

A normal characteristic of hair growth in mammals, including humans, is that in most cases, the rate of hair growth and the length of its growth cycle are reduced with age. Those phenomena are common to all mammals with rare exceptions, and they must be differentiated from true male pattern alopecia, which is caused by target organ sensitivity to androgens.

Several factors may influence the rate of hair growth. These factors include race, sex, age, geography, season of the year, nutrition and hormones. See Myers, R. J. and Hamilton, J. B. "Regeneration and rate of growth of hairs in man" *Ann. N.Y. Acad. Sci.* 53:562–568 (1951); Hamilton, J. B. "Age, sex and genetic factors in the relation of hair growth in man: A comparison of Caucasian and Japanese populations" *The Biology of Hair Growth* (Ed. Montagna, W. and Ellis, R. A.), Academic Press Inc., New York, pp. 400–433 (1958); Yano, S. "Rate of hair growth" *Hifu to Hinyo* 4:546–552 (1936); Maeda, I. "Study on the cuticula of hair: (III) Relation between the cuticula and rate of the growth of human hair" *Jyuzenkai-Zasski*, 43:1298–1304 (1938); Trotter, M. "The resistance of hair to certain supposed growth stimulants" *Arch. Dermatol. and Syphilol.* 7:93–98 (1923); Pinkus, F. "Zur Kenntnis der Lebensdauer der menschlichen terminal haare" *Z. Morphol. und Anthropol.* 24:256–269 (1924); Ono, M. "Studies on the hair growth of beard and scalp hair (1st report) Influencing factor in the rhythms of hair growth" *J. Physiol. Soc. Japan* 25:254–261 (1963).

Various preparations have heretofore been proposed for the treatment of male pattern baldness. It is also a matter of common knowledge, however, that none of the so-called "hair growth formulae" have proven to be very efficacious.

In contrast to most epithelial structures, the hair follicle does not grow continuously throughout its life, but passes through a cycle called the pilar cycle. The pilar cycle comprises essentially three phases—namely, the anagen or growth phase during which hair is produced, normally lasting about three to seven years; the catagen phase when growth stops and the follicle atrophies, lasting about three to four weeks; and the telogen phase, which is a rest period for the follicle during which the hair progressively separates and finally falls out, and normally lasting about three to four months. Normally 80 to 95 percent of the follicles are in the anagen phase, less than 1 percent being in the catagen phase, and the rest being in the telogen phase. Whereas the telogen phase hair is uniform in diameter with a slightly bulbous, non-pigmented root, the anagen phase hair has a large colored bulb at its root.

Alopecia results when the pilar cycle is disturbed, resulting in excessive hair loss. The most frequent phenomenon is a shortening of the hair growth phase due to cessation of cell proliferation. This results in an early onset of the catagen phase, and consequently a large number of hairs in the telogen phase during which the follicles are detached from the dermal papillae, and the hairs fall out. This shortening of the growth or anagen phase of the pilar cycle may have different origins, among which are very diverse pathological origins such as febrile conditions, mental stresses, hormonal problems (such as androgenetic alopecia due to male hormones) and secondary effects of drugs. Alopecia may also be due to age and to a slowing down of mitotic activity. This dysfunction of the biological mechanism of hair growth leading to alopecia may be regarded as a disease. While there are other causes of alopecia such as greasy or oily scalp due to seborrhea and the dandruff accompanying it, the present invention is not directed to treating these extraneous causes of alopecia, but rather to treating the organic dysfunction of the hair follicle.

German Patent No. 2758484 discloses certain chemical preparations for treatment of scalp to prevent baldness. These preparations contain bile compounds as the active ingredients and also include pro Vitamin A or tretinoin. The active ingredient is a product obtained from gall or a derivative thereof such as chenodeoxycholic acid, urodoxy cholic acid and their salts or derivatives.

Another patent is Olsen U.S. Pat. No. 4,140,229 citing the use of Vitamin A-containing crystal clear, transparent, aqueous, sprayable emulsions for reducing itching and flaking of common dandruff and seborrhea. As stated in its abstract, in some instances, the use of such emulsions reduced excessive falling hair. It does not purport to stimulate hair growth. It simply teaches a method of conditioning hair and scalp to effect relief from dandruff symptoms. The only pertinent example in Olson is discussed under Case History No. 3 of Example IV wherein the "Spray-on-Brush-in-Solution" contained Vitamin A palmitate and seven other ingredients. All that is disclosed is that "the daily loss of head hair was reduced to approximately 10 to 20."

Knight British patent specification No. 1,466,062 discloses a cosmetic composition containing tocopherol and retinoic acid as a cosmetic preparation which can be used on the skin or as a hair cleaning or hair dressing agent. This multi-purpose cosmetic composition allegedly prevents age spots, and is claimed to be good for clearing the scalp of dandruff. It appears that, during clearing of the scalp of dandruff with this composition, the scalp can become healthier, hair loss is reduced, and hair growth can recommence. A specific treatment for androgenetic alopecia or male pattern alopecia is not suggested by this disclosure. The use of retinoids to alter the hair follicle growth rate or to prolong the anagen phase of the hair cycle is also not disclosed or discussed by Knight. Knight is claiming a cosmetic lotion for cleaning the scalp. Common dandruff and seborrhea or seborrheic dermatitis (seborrhea is the production of excess sebum and seborrheic dermatitis is an irritation of the scalp), as well as age spots, are the topic of this patent, and the composition used is a combination of two ingredients (Vitamin E and retinoic acid) in a cosmetic base.

There is a reference in the literature to the treatment of monilethrix using tretinoin (retinoic acid). Monilethrix is a vary rare genetic disease in which the hair shaft is defective and the hair is sparse and fragile. Topical application of retinoic acid improved the symptoms of this genetic defect. Hernandez-Perez, E. "Tretinoin therapy for monilethrix" *Archives of Dermatology* 109:575–576 (1974).

The use of retinoic acid in many disease conditions has been recently reviewed in the *Journal of the American Academy of Dermatology* by Haas and Arndt, "Selected therapeutic applications of topical tretinoin" 15:870–877 (1986). The review article in the May 1981 *Journal of the American Academy of Dermatology*, by Thomas, et al. also gives a list of the known uses of retinoic acid, but the treatment of alopecia or androgenetic alopecia is not listed.

There are no references of which I am aware for the use of retinoids in altering the rate of hair growth or treating alopecias, such as androgenetic alopecia. In fact, quite the opposite is the case, and the literature is full of references to hair loss caused by the toxic use of retinoids in high concentrations. References to hair loss caused by retinoids include W. Bollag and A. Matter, "From Vit A to Retinoids in Experimental and Clinical Oncology", p. 9–23, *Modulation of Cellular Interactions by Vitamin A and Derivatives, (Retinoids)* (Eds. Luigi M. DeLuca, Stanley S. Shapiro) Annals of New York Academy of Sciences, Vol. 359 (1981) and *Retinoids: Advances in Basic Research and Therapy* (Eds. C. E. Orfanos) Springer-Verlag (1981)—See articles "Aromatic Retinoids in Psoriasis", p. 165–173, S. Jablouska, et al.; and "Treatment of Severe Forms of Psoriasis and Retinoic Acid Derivatives" J. C. Gatti, et al., p. 185–191.

BRIEF SUMMARY OF THE INVENTION

According to the invention it has been found that retinoids or mixtures thereof are effective in stimulating hair growth, increasing the rate at which hair grows on mammalian skin, prolonging the anagen phase of the hair cycle, and converting vellus hair to terminal hair growth by topical application to the hair and hair follicles and to the skin adjacent thereto. The invention is useful in the treatment of alopecias due to organic dysfunction of the hair follicle. Preparations such as lotions, creams, shampoos, and the like, containing the aforementioned compounds as the active ingredients, can be applied topically to the skin, hair and/or follicles for this purpose. Oral administration of the retinoids may also be used. Other adjunctive compounds which may be included in the compositions of the invention include vitamins, such as Vitamin $D_3$, hormones, antiandrogens, and vasodilators. The invention also includes the topical or oral administration of retinoids to fur bearing animals or birds to increase the rate of hair growth and/or retard shedding or molting.

DETAILED DESCRIPTION OF THE PREFERRED EMBODIMENT

It has been unexpectedly discovered that retinoids, when topically applied to mammalian skin in effective amounts, stimulate and increase the rate of hair growth on the scalp, prolong the anagen phase of the hair cycle and convert vellus hair to terminal hair growth. Moreover, these compounds can be effective in the treatment of certain types of alopecia. Typically, these compounds constitute the active ingredients of different types of preparations, such as lotions, solutions, ointments, creams, sprays, and the like.

The compounds of the present invention which form the active ingredients in these hair growth preparations include retinoids or pharmaceutically acceptable derivatives or analogs thereof, such as esters, amides, ethers or salts (e.g. acid addition salts), including all transretinoic acid and its stereoisomers, geometrical isomers, metabolites, derivatives, and new synthetic molecules related to retinoic acid because of their ability to bind to retinoid receptors within cells.

These retinoids may constitute the sole active ingredient of the preparations or formulations, or they may be used in combination with each other or in combination with adjunctive compounds. Such combinations may exhibit synergism in that they increase the rate at which hair grows or they may stimulate hair growth to a greater extent than the individual active ingredients of the combination alone.

While applicant does not wish to be bound by any particular theory, a major problem in influencing alopecia is to revascularize the area of the alopecia and initiate the primary new hair growth. Retinoids cause percutaneous absorption of themselves and other compounds, and they are very active in causing increased rate of hair growth. However, in certain advanced cases, it is difficult for retinoids alone to reverse the follicle atrophy. Certain compounds such as hormones, antiandrogens or vitamins, such as Vitamin $D_3$ compounds, are useful as adjuncts to retinoids in their stimulatory action on the hair follicle.

Suitable retinoid active ingredients for use in this invention include derivatives of retinoic acid (Vitamin A acid or tretinoin) which may be represented by the following formula:

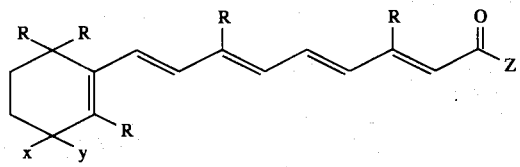

wherein R is hydrogen or a lower alkyl group, X is individually hydrogen and Y is individually hydrogen or a hydroxy group, or X and Y together form oxo, and Z is alkoxy, amine, alkylamide, hydroxy, nitro, or other suitable terminal groups. Also included by the above formula are pharmaceutically accepted salts thereof.

Further, the basic formula may include the dehydro, dihydro, or anhydro forms, such as the 7,8-dehydro and 5,6-dihydro forms, of retinoic acid as well as all of the stereoisomeric forms thereof, such as the 9-cis; 9,13-dicis; 13-cis; 11-cis; 11,13-dicis; etc. Examples are shown as follows:

13-cis-retinoic acid

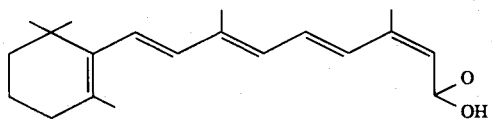

9-cis-retinoic acid

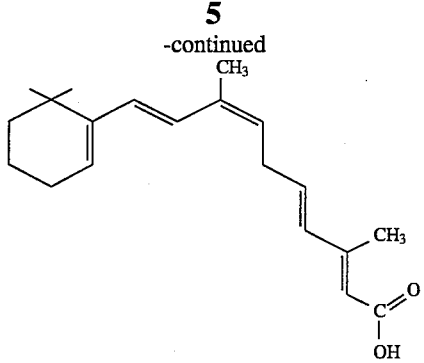

7, 8-dehydro-retinioc acid

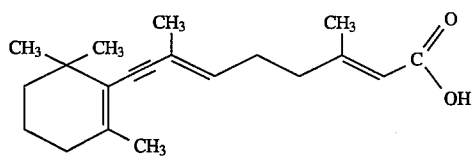

5, 6-dihydro-retinoic acid

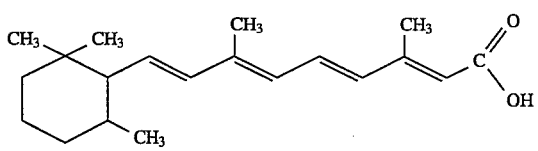

The anhydro forms may be represented by the following compounds:

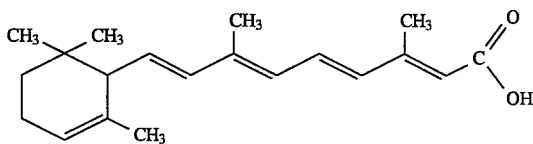

α-form

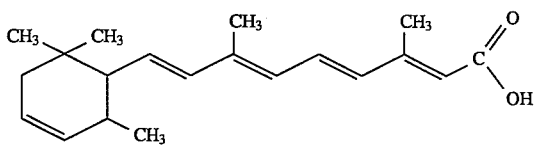

γ-form

Suitable retinoid analogs and derivatives useful in the invention have the following general formulae wherein the side chain, the ring, or both, may be altered:

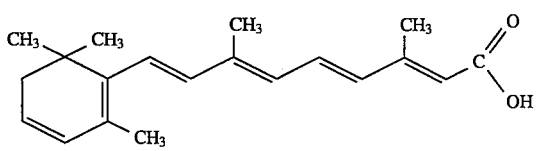

Vitamin A2 Acid

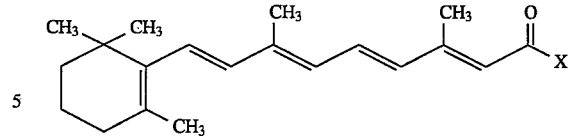

wherein X is a member selected from the group consisting of: —OHCH$_2$CONH$_2$: mixed —OCH$_2$CH(OH)CH$_3$ and —OCH(CH$_3$)CH$_{20}$H; —OCH$_2$CH$_2$OH; as well as

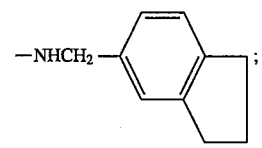

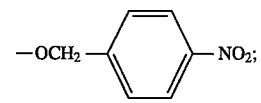

—OCH$_2$—C$_6$H$_5$; and

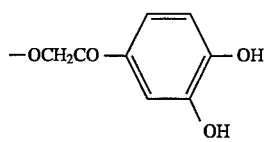

These compounds as well as other alkoxy and amide compounds can be active as they can be hydrolyzed to retinoic acid and other active compounds in the body. However, their activity may not be as direct as all-trans retinoic acid.

Other suitable retinoid compounds useful in the invention include α- hydroxy retinoic acid represented by the formula:

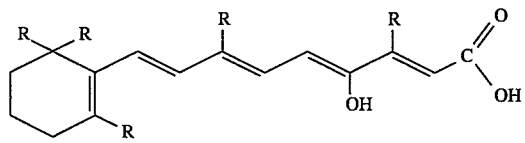

and the C$_{22}$-analog of retinoic acid represented by the following general formula:

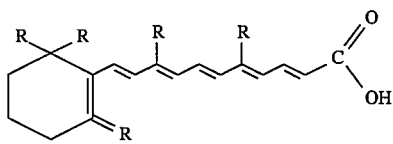

where R in both of the above formulae are lower alkyl radicals, preferably methyl groups.

Other structurally modified retinoic acids which, to some degree, exhibit the activity of retinoic acid for hair growth purposes can be represented by the following general formulae:

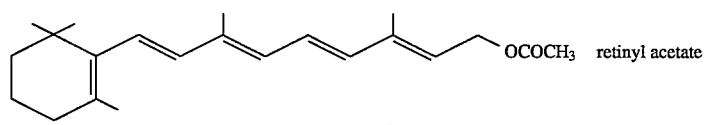

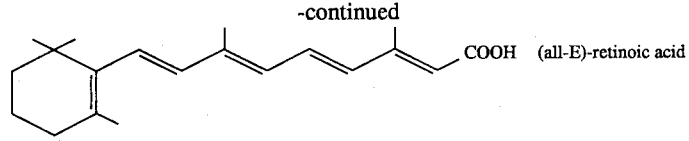
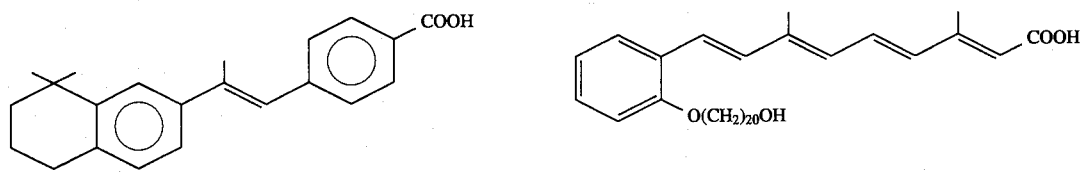
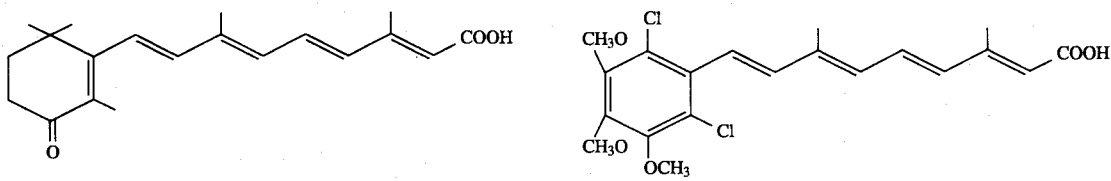
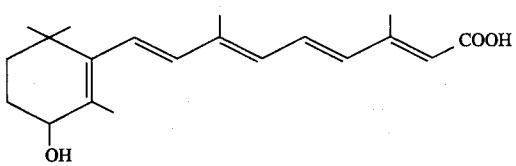
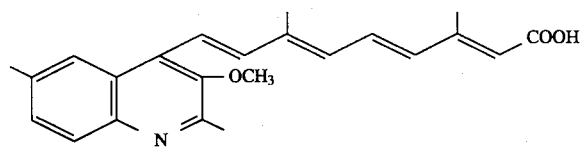
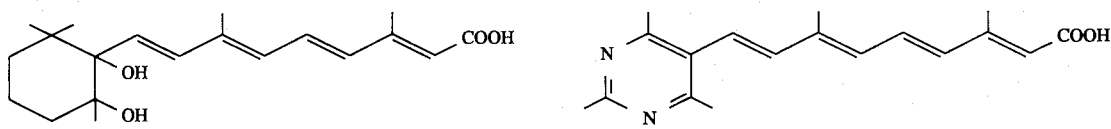
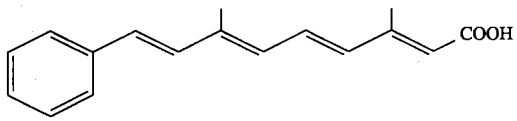
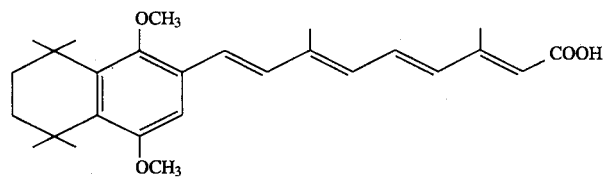
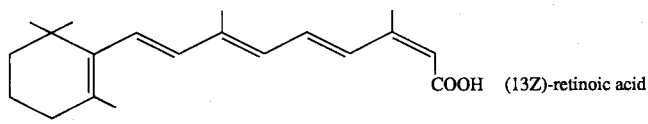
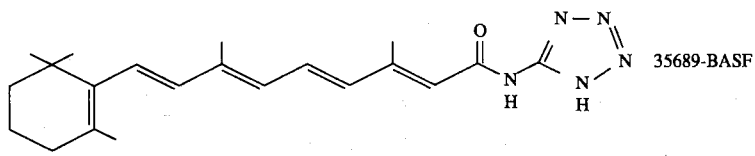
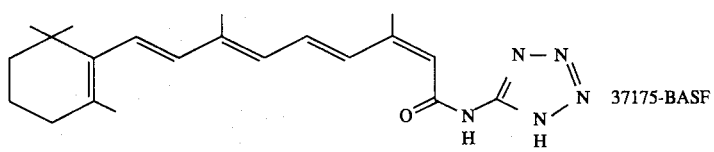

-continued
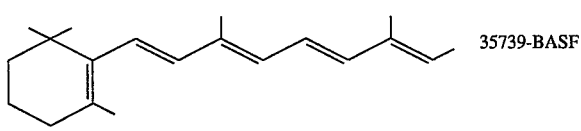 35739-BASF
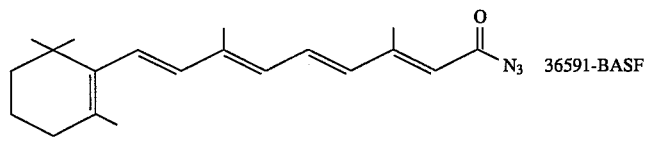 36591-BASF
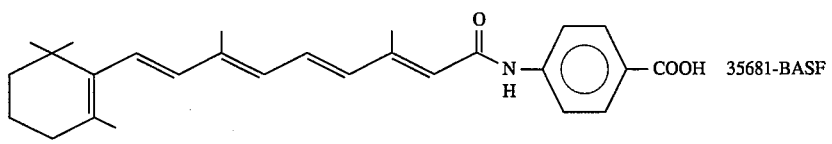 35681-BASF
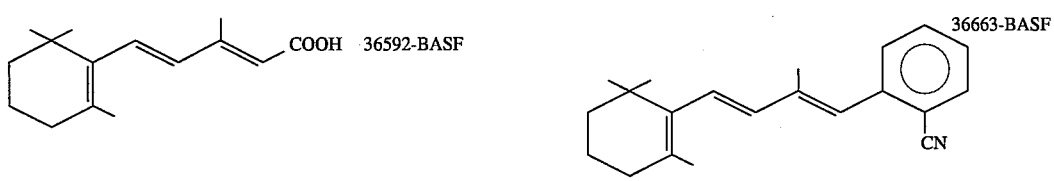
36592-BASF    36663-BASF
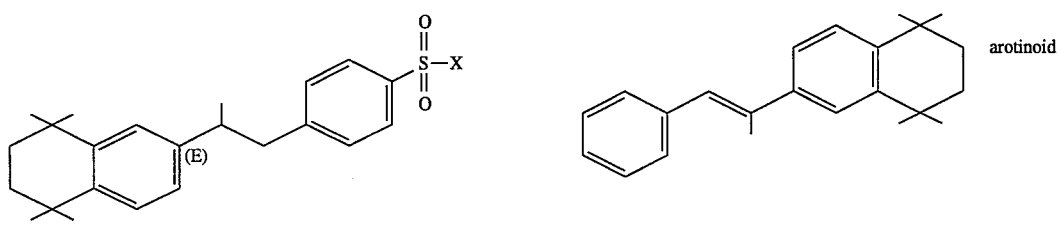
    arotinoid
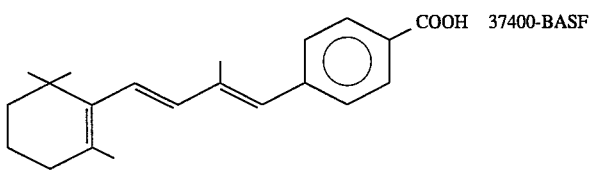 37400-BASF
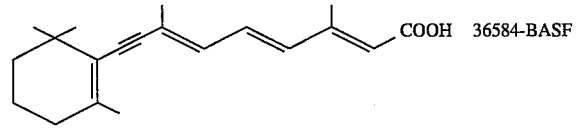 36584-BASF
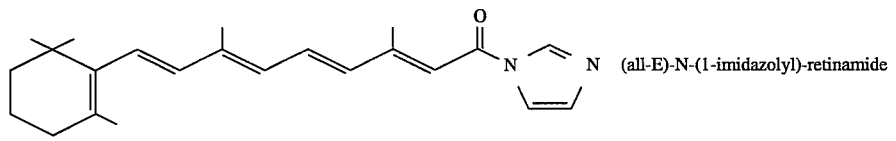 (all-E)-N-(1-imidazolyl)-retinamide
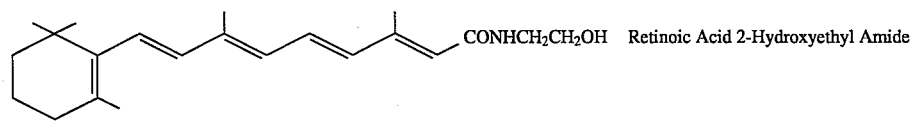 Retinoic Acid 2-Hydroxyethyl Amide
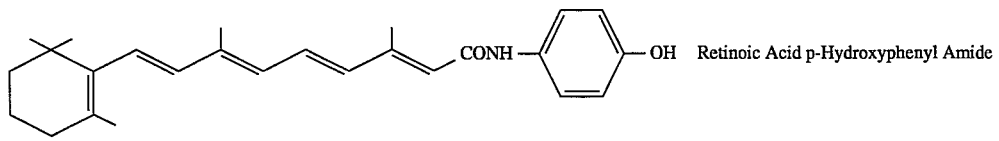 Retinoic Acid p-Hydroxyphenyl Amide -continued
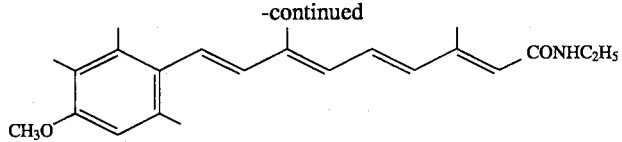
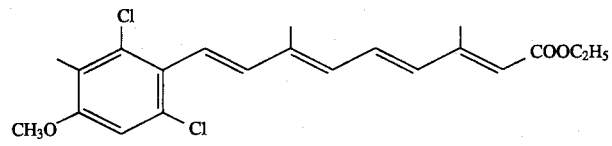
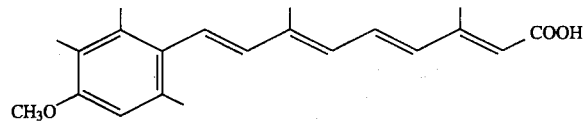
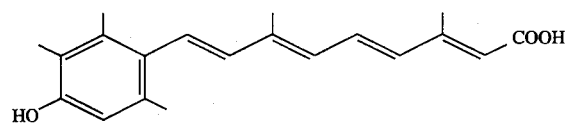
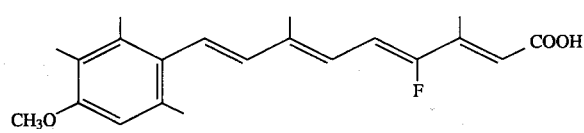
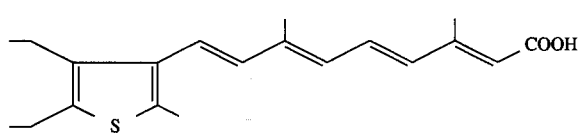
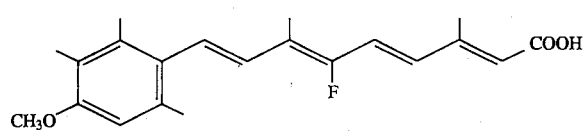
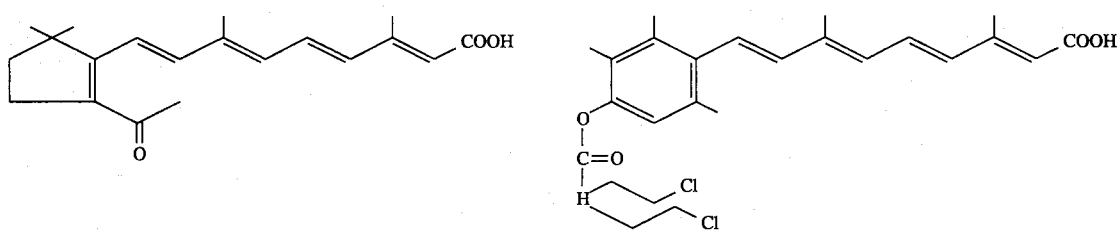
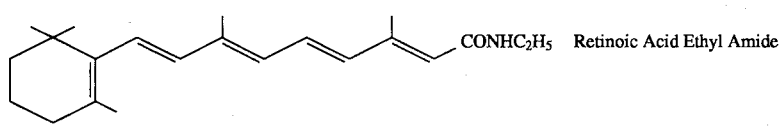 Retinoic Acid Ethyl Amide
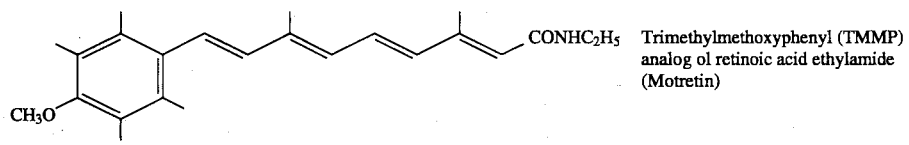 Trimethylmethoxyphenyl (TMMP) analog of retinoic acid ethylamide (Motretin)
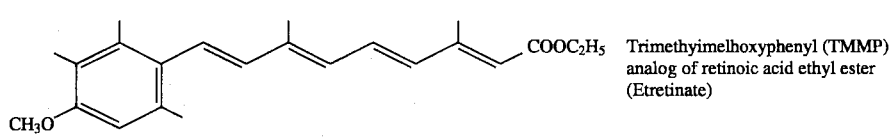 Trimethylmethoxyphenyl (TMMP) analog of retinoic acid ethyl ester (Etretinate)

-continued
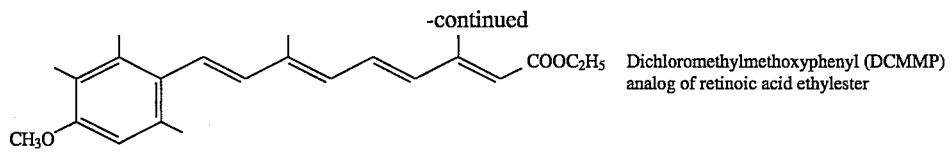
Dichloromethylmethoxyphenyl (DCMMP) analog of retinoic acid ethylester
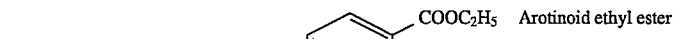
Arotinoid ethyl ester
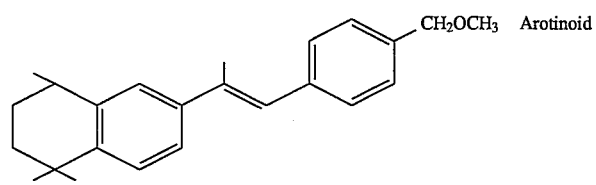
Arotinoid
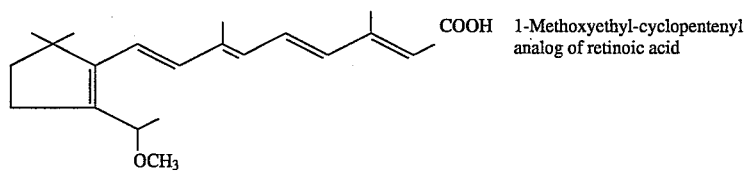
1-Methoxyethyl-cyclopentenyl analog of retinoic acid
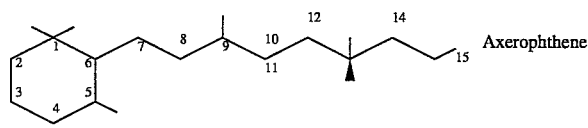
Axerophthene
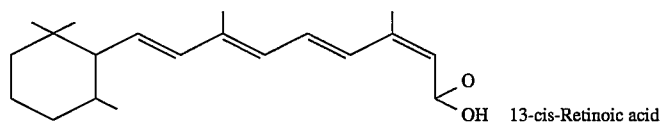
13-cis-Retinoic acid
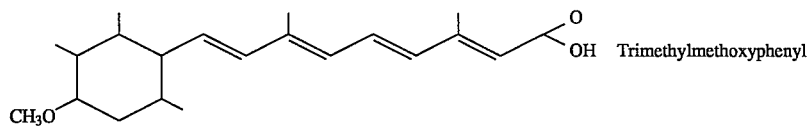
Trimethylmethoxyphenyl
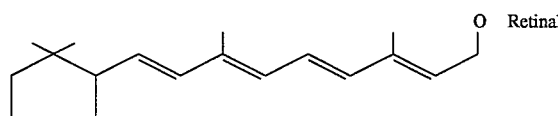
Retinal
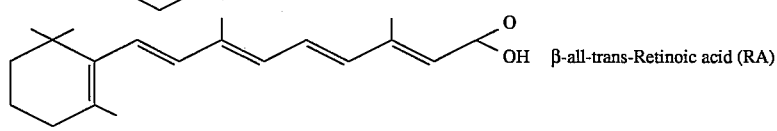
β-all-trans-Retinoic acid (RA)
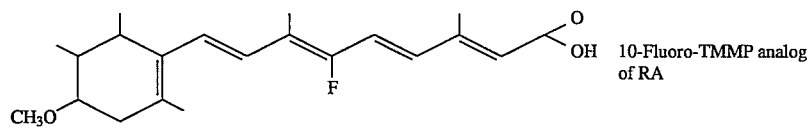
10-Fluoro-TMMP analog of RA
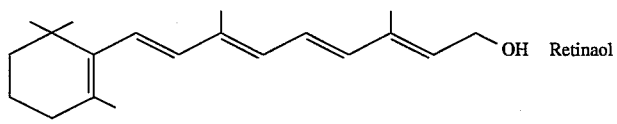
Retinaol

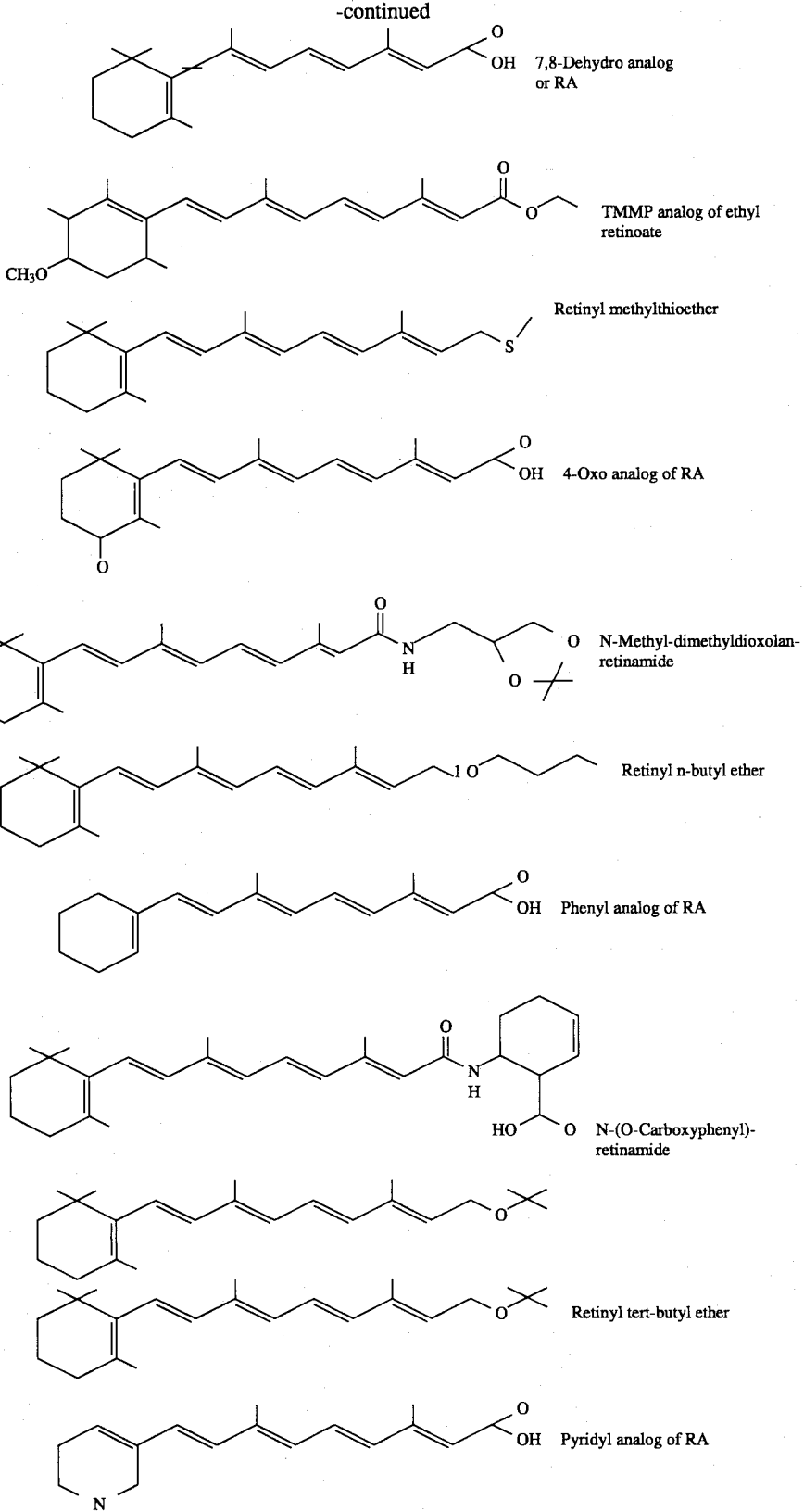

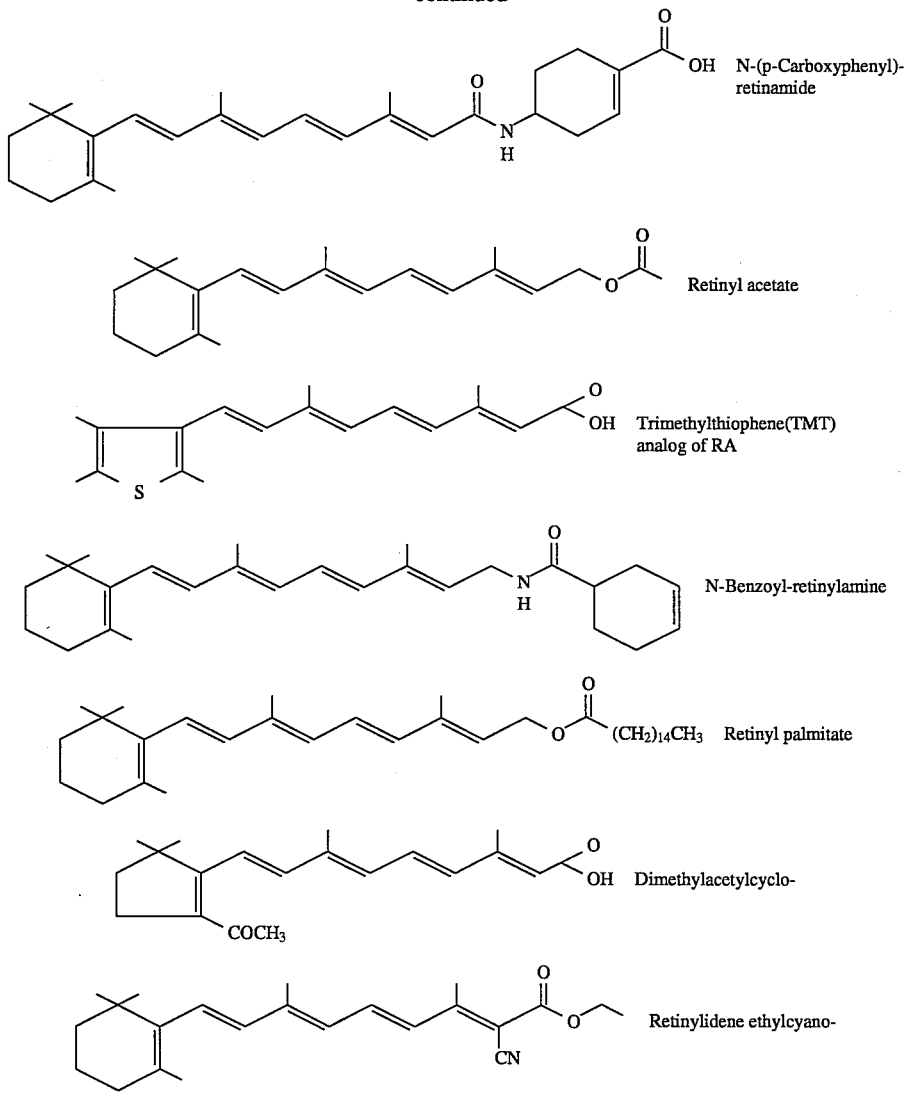
Still other useful analogs and derivatives of retinoic acid and retinoids include the following compounds:
BENZOTHIOPHENE
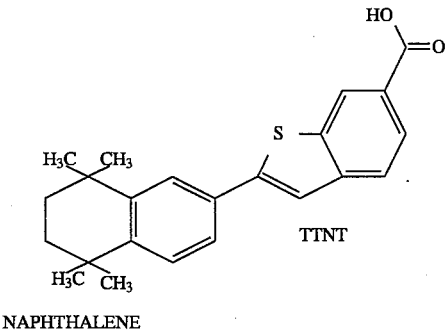
NAPHTHALENE
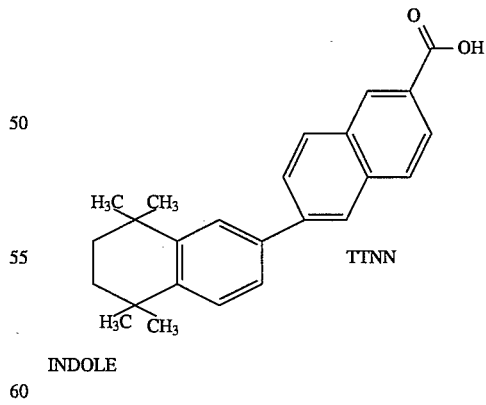
INDOLE

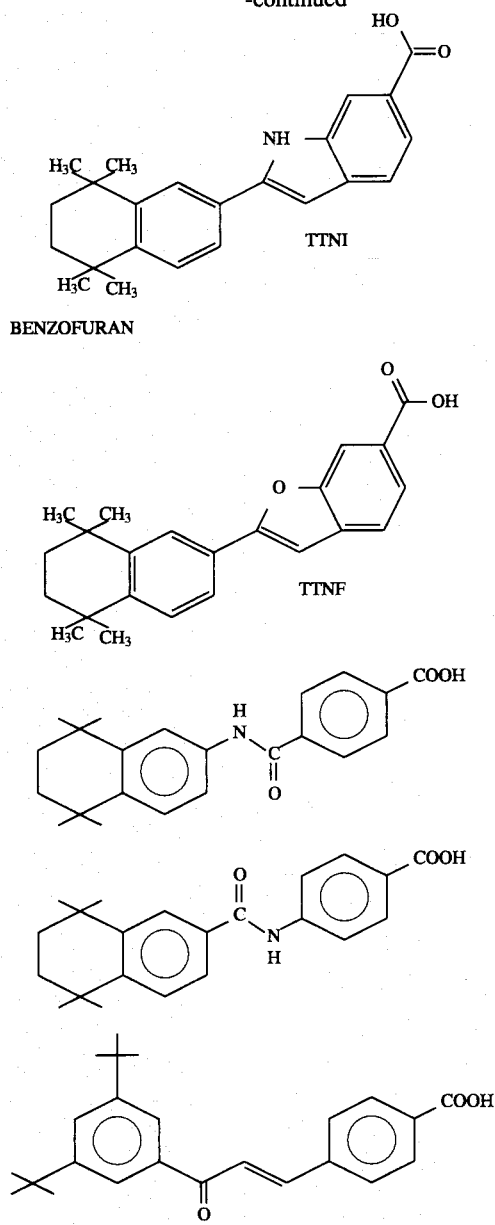

Also included within the foregoing compounds are any halogenated compounds or ether, amide, modified rings, dehydro, dihydro, isomer or analog forms of said compounds.

The retinoid compounds useful in the present invention are believed to have the common characteristic of binding to the retinoid cell receptors and thereby stimulating hair follicle cell proliferation.

Retinoids have been defined narrowly as comprising simply Vitamin A (retinol) and its derivatives such as Vitamin A aldehyde (retinal), Vitamin A acid (retinoic acid), comprising the so-called natural retinoids. Retinol and its esters have been used previously in hair preparations for preventing hair loss, but not to increase or stimulate hair growth in cases of alopecia.

Subsequent research has resulted in a much larger class of chemical compounds that are termed retinoids due to their biological similarity to Vitamin A and its derivatives. Compounds useful in the present invention include natural forms of Vitamin A, Vitamin A acid and its isomers, Vitamin A aldehyde and/or synthetic analogs of Vitamin A acid which possess the biological activity of Vitamin A acid in the hair follicle. Accordingly, as used herein for purposes of the present invention, the term "retinoid" will be understood to include any compound which fits the foregoing chemical and/or biological definitions.

That is, the definition of a retinoid intended in this invention is a substance that can elicit a specific biological response by binding to and activating a specific receptor or set of receptors for retinoic acid. Therefore, any Vitamin A type compound, whether defined by the classic description of a particular subset of diterpenoid, polyene substances or a new type of synthetic ligand (neither diterpenoid nor polyene) which can have a better molecular fit to the retinoid receptors (cytosolic retinoic acid binding proteins), should be considered in this definition. The biological response of the target cells for retinoids should be defined as any compound (retinoid) which is capable of stimulating the hair follicle cells to differentiate or to turnover more rapidly. This covers compounds traditionally related to retinoids, and it also covers compounds which are not diterpenoid types. The ring, the side chain, the terminal group or all of these can be altered. This definition would include even newer retinoids which do not fit the older Vitamin A-type concept but which can be shown to bind to the retinoid receptor proteins specific for retinoic acid (CRABP) within cells of the follicular epithelium. Examples of such newer retinoids include, inter alia, TTNT, TTNN, TTNI, TTNF, Am-80, Am-580 and Ch-55, which are shown above.

The retinoids, alone or in combination with the other adjunctive ingredients of this invention, cause elevated DNA synthesis in keratinocytes in the cell cultures. These compounds also increase the turnover time of epidermal cells in cell culture experiments as well as in in vivo experiments with human subjects. Surprisingly, it has been discovered according to the present invention that the cells of the hair follicle, including the papillae, can be stimulated by retinoids. When tested experimentally, the retinoids cause the cells of the dermal papillae and the cells of the root sheath to incorporate more tritiated thymidine into DNA and to reproduce at a more rapid rate than untreated cells from other hair follicles. This stimulation by the retinoid compounds ultimately causes the entire hair follicle to become more activated and the mitotic index, as measured by thymidine-$H^3$ incorporation into DNA, to rise. Therefore, the individual scalp hairs can be shown to grow at an increased rate, and the anagen phase is prolonged.

A major problem in influencing hair growth is obtaining good percutaneous absorption of the active compounds. The retinoid compounds described herein cause excellent percutaneous absorption and are very active on the keratinizing cells of the skin, including the hair follicles.

Accurate measurement of hair growth to substantiate the results of the testing is often a problem. A microcapillary method which gives excellent results and can be used to measure the rate of hair growth was devised by M. Saitoh, et al., *Advances in Biology of the Skin*, vol. 6, p. 467 (1968) and utilizes microcapillary tubes which are graduated using 0.2 mm graduations. A less time-consuming magnification method which also yields good results involves shaving off of the hairs at skin level and magnifying the cut-off hairs for examination and measurement.

The pharmaceutical, cosmetic or veterinary preparations of the present invention can be prepared by conventional techniques for the preparation of lotions, creams, conditioners or shampoos for the scalp or veterinary preparations for pelts. Though not as preferred, included also are preparations which can be administered orally and compounds which can be added to animal foods.

In addition to the active retinoids of this invention, the various preparations can contain any conventional pharmaceutically acceptable or cosmetically acceptable inert or pharmacodynamically active additives or carriers. For example, the lotions may be prepared using various forms of alcohols or other solubilizers such as glycols or esters. The conditioners may contain the normally acceptable, commercially produced compounds such as cetyl alcohol, cetearth-5, -20 hydantoins, hydrolyzed animal protein, glycol stearate, amodimethicone, paraffin, mineral oil, silicones, etc.

The topical compounds may also contain various adjunctive compounds, such as oils, including essential fatty acids; vitamins or their derivatives; hormones (natural or synthetic), including progesterones, estrogens including estradiols, thyroids, and polypeptide hormones; and antiandrogens, including but not limited to cyproterone acetate, cyoctol, secosteroids, flutamide or spironolactone, and particularly non-steroidal antiandrogens such as the decahydro-7H-benz(E)-inden-7-ones described in U.S. Pat. No. 4,466,971. Androgens are known to cause alopecia in genetically programmed individuals, and antiandrogens prevent the effect of the androgen on the nucleus of the hair follicle cell. Therefore, any substance which can prevent the androgen from acting on the nucleus of the cell is considered an antiandrogen.

Examples of the active-type Vitamin $D_3$ which can be used in combination with the retinoids of this invention include the following types which are not meant to be limiting: 1-hydroxycholecalciferol; 1,25-dihydroxycholecalciferol (commercially available as ROCALTROL); and 1,24dihydroxycholecalciferol. Vitamin $D_3$ is generally administered at a rate of about 0.001 to 0.3 ug/gm. Vitamin $D_3$ type compounds have recently been shown to regulate cell differentiation and to promote the differentiation of the keratinocyte. Vitamin D compounds are also important in calcium regulation and may therefore affect the hair follicle calcium balance. It is also believed that these compounds may assist in the conversion of vellus to terminal hairs.

Other important compounds, which in combination with the active retinoids of this invention, may further improve the rate of hair growth include vasodilators, particularly peripheral circulatory system vasodilators. Diminished or insufficient vascularization is a problem in some forms or cases of alopecia, and it is believed that vasodilators aid in hair growth and hair follicle stimulation by increasing the blood supply to the microvasculature around the hair follicle, thereby allowing more nutrients to enter the cells and more waste products or catabolites to be carried away.

Examples of vasodilators which may be used in combination with the retinoids of the present application include, for example, the following: 3-pyridinemethanol, 4-aminopyrrolo(2,3-d)pyrimidine, 2-(2methylaminoethyl)pyridine, thurfyl nicotinate, diazoxide, isoxsuprine, diltiazem, cetiedil, buterizine, viprostol, azaclorzine, nicarpidine, flunarizine, nisoldipine, hexobendine, nicorandil, N-(2-nitrooxyethyl)pyridine-carboxamide compounds (WO-8804-171-A), trimetazidine, thymoxamine, zolertine, tipropidil, 4,4-diphenyl-2-butylamine, suloctidil, mixidine, iproxamine, naftidrofuryl, nicersoline, nifedipine, cinepazet, 2-aminoethanol nitrate, oxprenolol, prenylamine, buphenine, bipyridamole, benziodarone, lidoflazine, nicametate, 2-phenyl-1-propylamine, oxpentifylline, pindolol, bamethan, butalamine, xanthinol, tris(2-nitroxyethyl)amine, papaverine or paperveroline, pentaerythritol, 3-methyl-1-butyl nitrite, heptaminol, 3-chloro-1,2-propanediol, 2-benzylimidazoline, oxyfedrine, vincamine, glycerol trinitrate, verapamil, imolamine, 3,3,5-trimethylcyclohexanol, prostacyclin and snythetic analogues thereof (such as iloprost, nileprost, ZK 36,374, and 7-fluoroprostacyclin derivatives described in GB Patent Specifications 2198130A and 2198131A), 11,15-dihydroxy-9-oxo-13-prostenoic acid, diethylstilboestrol, rutin, khellol, visnadin, cyclosporin, vasoactive intestinal polypeptides or lipids, cyclic AMP (acrasin), isobide, adenosine, mannitol, myo-inositol. Other suitable vasodilators include the substituted pyrimidine compounds disclosed in published PCT patent applications WO86/00616 and WO85/04577.

The topically applied lotions, creams, conditioners, or other formulations containing the retinoid will vary according to the standard art with regard to the amounts of other hydrophilic and hydrophobic ingredients, including emulsifiers and silicones, so that either an oily, semi-oily or oil-free product may be obtained. The shampoos may contain any of the conventionally used detergents or soaps and any other compounds used by those familiar with the art. Oil-based shampoos are included in these formulations.

The oral preparations may be tablets, liquids, capsules, etc. The pharmaceutically acceptable substances commonly used as preservatives, stabilizers, moisture retainers, emulsifiers, etc., can be present in these preparations. Conventionally acceptable antioxidants such as tocopherols, N-methyl 2-tocopheramine, butylated hydroxyanisole (BHA) and butylated hydroxytoluene (BHT), can be incorporated also in the preparations described herein.

The retinoids are administered in effective amounts, which vary with the mode of administration and the requirements of the subjects. For example, the topical treatments may consist of lotions, creams, conditioners, shampoos, oil treatments, etc., with about 0.0001 to 5% by weight of the active ingredients, i.e., all-trans retinoic acid, its analogs, or other retinoids as the preferred dosages of these compounds. Arotinoids may be effective used at doses as low as 0.00001% by weight or even lower.

The effectiveness of the active ingredients of this invention for increasing the rate of or stimulating hair growth will now be illustrated by the following examples. These examples, however, are merely representative and should not be construed so as to limit the scope of the invention.

EXAMPLES I–X

The experimental procedures in all examples were as follows. In the case of topical administration, a lotion containing 0.1 percent by weight of all-trans retinoic acid (or various other concentrations depending on the retinoid) was included in the preparation to be tested. As the vehicle, 5 weight percent propylene glycol, 1 mg per 100 ml butylated hydroxytoluene (BHT), and 95 weight percent ethanol were mixed in a beaker for several minutes at ambient conditions to obtain a homogeneous preparation in which the retinoid was dissolved. This lotion was labelled A and was the active drug preparation. A similar lotion was prepared by the foregoing procedure containing all the aforementioned ingredients, but omitting the retinoid. This preparation was labelled B and was the placebo lotion.

Volunteer subjects had a 3 to 4 cm diameter area of scalp hair bleached at the scalp end. The subjects were asked to apply the (placebo) lotion B, 2 times a day, to the scalp for varying periods of time from 10 to 30 days. The rate of hair growth in each individual was determined using measurements taken with either microcapillary measuring equipment or by magnification measurements. The rate of new hair growth from the scalp end to the bleached area was recorded every three to six days. The data is expressed as control rate of hair growth in mm of growth per day.

At the end of the placebo treatment, anagen/telogen ratios were determined by the following standard method of Orentreich, N. and Berger, R. A. "Selenium disulfide shampoo", *Arch. Derm.* 90:76–80 (1964): Hair plucking was done from the areas treated before and after treatment. A large surgical-needle-holding clamp, with jaws covered with a smooth layer of rubber was used. Twenty to fifty hairs were grasped at one time, approximately 1.0 cm above the scalp surface, and epilated with a single forceful pull. The hair roots and lower portion of the shafts were then cut off into shallow plastic Petri dishes, previously gridded into 1 cm squares, moistened with tap water, and examined and counted by transmitted light with a low-power dissecting microscope. The roots could also be stained to help in the interpretation.

Following the placebo treatment, the subjects were given lotion A (containing the active drug) or lotion B and asked to apply the lotion in the same manner in which they had applied the previous (placebo) lotion. The same procedure was followed for measuring hair growth, namely every three to six days the subject returned for measurements to determine rate of hair growth. At the end of the active drug treatment period, subjects again had anagen/telogen ratios determined. Neither the subjects nor the observers were told which lotion A or B was the active preparation until after the data were analyzed.

Before treatment and at monthly intervals thereafter, a circle 1 inch in diameter was drawn over the balding spot of the vertex with a skin marker and a template. The center of the circle was located by a three-point measurement, using the midpoint between the ears and a fixed distance from the base of the nose. These measurements were recorded at each visit. With the aid of a magnifying lens, the hairs in the 1-inch diameter circle were counted and typed as vellus hairs, indeterminate hairs, or terminal hairs. Nonpigmented short hairs were defined as vellus; pigmented hairs ranging from thin and short to slightly longer and thicker were defined as indeterminate. Hairs of the same color and bore diameter as those in adjacent nonbalding areas were classified as terminal. The count was repeated several times and the average used as the final count. The number of vellus and terminal hairs were compared before, during and at the final visit, and calculated as percent conversions from vellus hairs to terminal hair growth.

The results of these experiments are expressed in Tables I through X, below. The results in the tables show that the use of retinoid preparations increase the rate of hair growth. In addition, treatment with these compounds, as shown in the tables, prolongs the anagen phase of the hair cycle and more hairs were found in the anagen phase than during the placebo treatment. Unless otherwise indicated, the topical applications used the lotion vehicle described above. The topical cream was a formula as in Formulation Example III below, and the oral administration was by tablet as in Formulation Example IV below.

TABLE I 0.1% All-Trans Retinoic Acid

| Subject Sex | Age | Dosage (mg/day) | Form of Dosage | Treatment Time (days) | Rate of Growth (mm/day) Control (Lotion B) | Treatment (Lotion A) |
|---|---|---|---|---|---|---|
| M | 36 | 10 | Topical | 21 | 0.30 | 0.45 |
| M | 38 | 60 | Oral | 14 | 0.21 | 0.25 |
| M | 24 | 10 | Topical | 10 | 0.35 | 0.49 |
| F | 35 | 10 | Topical | 30 | 0.39 | 0.50 |
| F | 41 | 60 | Oral | 28 | 0.36 | 0.39 |
| F | 63 | 10 | Topical | 21 | 0.28 | 0.38 |

TABLE II 0.1% All-Trans Retinoic Acid Ethyl Ester

| Subject Sex | Age | Dosage (mg/day) | Form of Dosage | Treatment Time (days) | Rate of Growth (mm/day) Control (Lotion B) | Treatment (Lotion A) |
|---|---|---|---|---|---|---|
| M | 31 | 10 | Topical | 21 | 0.25 | 0.31 |
| M | 68 | 10 | Topical | 20 | 0.21 | 0.29 |
| M | 38 | 40 | Oral | 21 | 0.30 | 0.32 |
| F | 36 | 10 | Topical | 22 | 0.34 | 0.46 |
| F | 42 | 10 | Topical Cream | 19 | 0.31 | 0.40 |
| F | 66 | 40 | Oral | 20 | 0.28 | 0.29 |

TABLE III 0.1% All-Trans Retinaldehyde

| Subject Sex | Age | Dosage (mg/day) | Form of Dosage | Treatment Time (days) | Rate of Growth (mm/day) Control (Lotion B) | Treatment (Lotion A) |
|---|---|---|---|---|---|---|
| M | 36 | 10 | Topical | 21 | 0.30 | 0.35 |
| M | 38 | 10 | Topical | 14 | 0.23 | 0.32 |
| M | 24 | 10 | Topical | 10 | 0.35 | 0.40 |
| F | 35 | 10 | Topical | 30 | 0.39 | 0.45 |
| F | 41 | 10 | Topical | 28 | 0.31 | 0.35 |
| F | 63 | 10 | Topical | 21 | 0.28 | 0.41 |

TABLE IV 0.1% All-Trans Retinoyl Acetate

| Subject Sex | Age | Dosage (mg/day) | Form of Dosage | Treatment Time (days) | Rate of Growth (mm/day) Control (Lotion B) | Treatment (Lotion A) |
|---|---|---|---|---|---|---|
| M | 36 | 10 | Topical | 21 | 0.30 | 0.45 |

TABLE IV-continued

0.1% All-Trans Retinoyl Acetate

| Subject | | Dosage | Form of | Treatment Time | Rate of Growth (mm/day) | |
|---|---|---|---|---|---|---|
| Sex | Age | (mg/day) | Dosage | (days) | Control (Lotion B) | Treatment (Lotion A) |
| M | 38 | 60 | Oral | 4 | 0.21 | 0.20 |
| M | 24 | 10 | Topical | 10 | 0.35 | 0.41 |
| F | 35 | 10 | Topical | 30 | 0.39 | 0.39 |
| F | 41 | 60 | Oral | 2 | 0.30 | 0.30 |
| F | 63 | 10 | Topical | 21 | 0.28 | 0.39 |

TABLE V

0.1% All-Trans Retinamide

| Subject | | Dosage | Form of | Treatment Time | Rate of Growth (mm/day) | |
|---|---|---|---|---|---|---|
| Sex | Age | (mg/day) | Dosage | (days) | Control (Lotion B) | Treatment (Lotion A) |
| M | 31 | 10 | Topical | 21 | 0.25 | 0.30 |
| M | 68 | 10 | Topical | 20 | 0.21 | 0.20 |

TABLE VI

0.1% δ-Retinoic Acid

| Subject | | Dosage | Form of | Treatment Time | Rate of Growth (mm/day) | |
|---|---|---|---|---|---|---|
| Sex | Age | (mg/day) | Dosage | (days) | Control (Lotion B) | Treatment (Lotion A) |
| M | 36 | 10 | Topical | 22 | 0.34 | 0.40 |
| M | 42 | 10 | Topical Cream | 19 | 0.31 | 0.41 |

TABLE VII

0.1% 9,13-Dicis Retinoic Acid

| Subject | | Dosage | Form of | Treatment Time | Rate of Growth (mm/day) | | % Conversion Vellus to |
|---|---|---|---|---|---|---|---|
| Sex | Age | (ml/day) | Dosage | (Months) | Control (Lotion B) | Treatment (Lotion A) | Terminal |
| M | 25 | 10 | Topical | 2 | 0.29 | 0.32 | 9% |
| M | 28 | 10 | Topical | 2 | 0.32 | 0.35 | 11% |
| M | 39 | 10 | Topical | 2 | 0.31 | 0.30 | 12% |
| F | 42 | 10 | Topical | 2 | 0.29 | 0.29 | 8% |
| F | 51 | 10 | Topical | 2 | 0.35 | 0.38 | 10% |
| F | 56 | 10 | Topical | 2 | 0.33 | 0.39 | 11% |

TABLE VIII

0.1% 11-Cis Retinoic Acid

| Subject Sex | Age | Dosage (ml/day) | Form of Dosage | Treatment Time (Months) | Rate of Growth (mm/day) Control (Lotion B) | Rate of Growth (mm/day) Treatment (Lotion A) | % Conversion Vellus to Terminal |
|---|---|---|---|---|---|---|---|
| M | 47 | 10 | Topical | 2 | 0.25 | 0.27 | 9% |
| M | 43 | 10 | Topical | 2 | 0.31 | 0.31 | 10% |
| M | 42 | 10 | Topical | 2 | 0.27 | 0.28 | 10% |
| F | 36 | 10 | Topical | 2 | 0.29 | 0.30 | 11% |
| F | 28 | 10 | Topical | 2 | 0.32 | 0.32 | 8% |
| F | 32 | 10 | Topical | 2 | 0.26 | 0.29 | 13% |

TABLE IX

0.1% 9-Cis Retinoic Acid

| Subject Sex | Age | Dosage (ml/day) | Form of Dosage | Treatment Time (Months) | Rate of Growth (mm/day) Control (Lotion B) | Rate of Growth (mm/day) Treatment (Lotion A) | % Conversion Vellus to Terminal |
|---|---|---|---|---|---|---|---|
| M | 37 | 10 | Topical | 2 | 0.28 | 0.29 | 10% |
| M | 35 | 10 | Topical | 2 | 0.31 | 0.35 | 8% |
| M | 41 | 10 | Topical | 2 | 0.27 | 0.27 | 5% |
| F | 39 | 10 | Topical | 2 | 0.30 | 0.33 | 7% |
| F | 45 | 10 | Topical | 2 | 0.26 | 0.28 | 9% |
| F | 58 | 10 | Topical | 2 | 0.23 | 0.27 | 12% |

TABLE X

0.1% 13-Cis Retinoic Acid

| Subject Sex | Age | Dosage (ml/day) | Form of Dosage | Treatment Time (Months) | Rate of Growth (mm/day) Control (Lotion B) | Rate of Growth (mm/day) Treatment (Lotion A) | % Conversion Vellus to Terminal |
|---|---|---|---|---|---|---|---|
| M | 35 | 10 | Topical | 2 | 0.28 | 0.31 | 7% |
| M | 72 | 10 | Topical | 2 | 0.21 | 0.25 | 9% |
| M | 38 | 10 | Topical | 2 | 0.26 | 0.28 | 12% |
| F | 65 | 10 | Topical | 2 | 0.24 | 0.27 | 11% |
| F | 42 | 10 | Topical | 2 | 0.29 | 0.32 | 7% |
| F | 39 | 10 | Topical | 2 | 0.31 | 0.33 | 10% |

Comparative Study I

A group of twenty normotensive subjects, twenty to sixty-four years of age and clinically diagnosed as suffering from androgenetic alopecia, were entered into a combined study in which twelve subjects received 0.025% topical tretinoin solution with the same vehicle as discussed above (95% ethanol, 5% propylene glycol and 1 mg BHT per 100 ml), five subjects received the vehicle alone as a placebo, and three subjects received 0.5% minoxidil solution alone, according to the following protocol. Food coloring was added to the placebo and minoxidil solutions to match the color of retinoic acid.

The subjects were instructed to apply 1 ml of the solution twice daily by dropper to the affected scalp area (a circular area of baldness, 1 inch in diameter). The subjects were advised to wear a cap for protection from the sun or to refrain from excessive sun exposure, and to avoid trauma to the scalp (i.e., vigorous scalp scrubbing or brushing). Blood pressure, serum chemistry tests, complete blood counts, weight, pulse and electrocardiogram were performed before treatment and at repeated intervals for each patient; skin irritation was assessed during each follow-up visit; photographs were taken before and during treatment to evaluate hair growth; and hair counts were performed initially, at monthly intervals, or at follow-up visits.

After analysis of the data, the subjects were placed into one of three designated response groups, with percent increase in number of terminal hairs (defined as thick, pigmented hairs, comparable to those on the subjects' posterior scalp) being the primary criterion for placement. Participants in the "good" response group (Group A) experienced greater than 46% increase in the number of hairs in the target area after treatment; individuals in the "moderate" response group (Group B) had a post-therapy terminal hair increase between 21% and 45%; while participants in the "no response" group (Group C) experienced increases below 20%. The mean amount of time for subject participation was 10, 8 and 9 months, respectively, for Groups A, B and C, and the results are indicated in Table XI below.

TABLE XI

| Treatment | No. of Patients | Response | | |
|---|---|---|---|---|
| | | Good (Group A) | Moderate (Group B) | None (Group C) |
| Placebo | 5 | 0. | 0 | 5 (100%) |
| Minoxidil | 3 | 0 | 0 | 3 (100%) |
| Tretinoin | 12 | 2 (16%) | 5 (42%) | 5 (42%) |

As shown in Table XI, 58% of the subjects who received tretinoin alone (7 women and 5 men) responded positively to the treatment with mostly moderate hair growth. Of the three individuals treated with 0.5% minoxidil, none showed terminal hair growth, but vellus hair growth was noted in one patient. There was no visible hair regrowth in patients receiving placebo.

Some interesting and noteworthy observations were made about selected patients in these studies, including: (1) one woman using tretinoin only experienced an 1,100% increase in hair growth. This 43 year old woman had had extensive androgenetic alopecia since she was 20 years old, and her increased hair growth took place in 18 months; (2) one man experienced prominent vellus hair growth in response to retinoic acid treatment after six months; (3) another male patient had previously received a series of hair transplants but discontinued that treatment because of poor hair growth in the transplanted plugs. During the course of his treatment with retinoic acid, growth was initiated in the transplanted grafts and regular hair trimming was required. Further details of this study, including photographs of some of the patients, can be found in Bazzano et al., "Topical Tretinoin for Hair Growth Promotion," *Journal of the American Academy of Dermatology*, 15:4, Pages 880–883 and 889–893 (October 1986).

Comparative Study II

Using essentially the same test procedure as Comparative Study I above, 15 male patients (ages 20 to 45) were entered into a year-long, double-blind study under the approval and review of the Institutional Review Committee on the Use of Human Subjects. The 15 subjects were randomized into two groups, 8 on active medication (0.025% retinoic acid in the vehicle described previously), and 7 on the placebo (vehicle alone). After six months, patients on placebo were switched to the active medication.

The 7 patients on placebo showed changes in numbers of vellus, terminal and indeterminate hair which were within the limits of normal variability, namely plus or minus 20% in the test area. Of the 8 patients on the retinoic acid medication, 4 patients showed a greater than 20% increase in terminal hairs in the test area. Of the 5 placebo patients who were switched to the retinoic acid medication after the initial six month period on placebo, 3 also showed increases of greater than 20% in total numbers of new terminal hairs in the test area six months after being switched to the active medication.

Prolongation of the Anagen Phase of the Hair Cycle

The prolongation of the anagen phase of the hair cycle may be demonstrated by examining anagen/telogen ratios before and during or after treatment. In a subsample of the patient population (20 patients) treated with retinoic acid according to the present invention, plucked hair counts of anagen and telogen hairs were made just before treatment and after three months of topical retinoic acid application. The plucked hair count results showed that the average amount of telogen hairs in the sample fell from 14% plus or minus 2% before the treatment to 9% plus or minus 3% after three months of treatment. These results demonstrate that the anagen phase of the hair cycle is being prolonged since a smaller percentage of hairs is in the telogen (inactive or non-growing) phase, and a larger percentage of hairs is found in the anagen (growth) phase.

The following examples illustrate typical formulations for use in the topical application or oral administration of retinoids according to the present invention.

FORMULATION EXAMPLE I

Topical Lotion

| Components | Weight % |
|---|---|
| Active Ingredient: All-trans retinoic acid | 0.01 to 0.1 |
| Ethanol | q.s. to 100.0 |
| Propylene glycol | 5.0 |
| Butylated hydroxytoluene (BHT) | 0.1 |
| Isopropyl myristate | 1.0 |

FORMULATION EXAMPLE II

Topical Cream Conditioner or Shampoo

| Components | Weight % |
|---|---|
| Active Ingredient: All-trans retinoic acid or 13-cis retinoic acid | 1.0 |
| Distilled water | q.s. to 100.0 |
| Cetrimonium Chloride | 5.0 |
| Cetyl alcohol | 4.0 |
| Ethanol | 4.0 |
| Butylated hydroxytoluene | 1.0 |
| Hydrolyzed animal protein | 0.5 |
| Methylparaben, propylparaben | 0.1 |

In this example, a higher concentration of active ingredient was used since the conditioner is rinsed out shortly after application.

FORMULATION EXAMPLE III

Topical Ointment 0.01, 0.025, 0.05 or 0.1 gram of retinoic acid is dissolved in 10 ml of acetone, and the solution admixed with 90 gram of USP grade hydrophilic ointment to a uniform consistency. One gram of butylated hydroxytoluene is then added to this mixture. A water-washable cream ointment is thus prepared.

FORMULATION EXAMPLE IV

Oral Tablets

| Components | Weight (mg) |
| --- | --- |
| Active Ingredient: All-trans retinoic acid or ethyl ester or acetate | 25 |
| Lactose | 52 |
| Cornstarch | 20 |
| Microcrystalline Cellulose | 40 |
| Talc | 2.5 |
| Magnesium stearate | 0.5 |

The active ingredients are mixed with lactose and granulated using a cornstarch paste. The remainder of the above adjuvants are then admixed therein, and the mass is tableted. The tablets are then coated with a water-soluble or water-swellable lacquer. Liquids, syrups or other formulations can be made consistent with pharmaceutical art.

The retinoids of the invention may also be used in veterinary preparations or feeds to increase the rate of growth of fur (pelt) in certain fur bearing animals and to retard shedding and molting.

In fur bearing animals, the rate of fur growth, length of hair, thickness of hair and molting season are controlled by many factors including season, light (wavelength) periodicity, temperature, hormonal factors and nutrition. Controlling all of these variables is impossible. However, animals were selected and areas over the hind quarters were shaved in 2 inch diameter circular areas. In some of the animals the areas were treated topically with all-trans retinoic acid, and in other animals the retinoid was administered orally in animal chow. Some of the animals served as their own controls, using treated and non-treated areas.

In fur bearing animals, the guard hairs and the pile hairs differ in thickness, length and growth rate. In the rabbits studied, the guard hairs averaged 34 mm and the pile hairs 30 mm in length. The effect of topical application of all-trans retinoic acid was to increase the rate of new hair growth. An effect on the non-shaved fur bearing areas treated with topical all-transretinoic acid in lotion form, was a decrease in the shedding or molting of fur. The mean rate of hair (fur) growth from treated shaved areas was 0.3 mm per day for 3 rabbits (mean) while in non-treatment shaved areas it averaged 0.2 mm per day (mean of 3 rabbits).

The effect could also be demonstrated in domestic cats and dogs; the same type of experimental procedures were used. The most striking effect in long haired dogs and cats was the retardation of molting or hair shedding. Long haired dogs and cats tended to retain more hair in the anagen phase and there was approximately 50% less shedding during the treatment periods. Both methods of administration were satisfactory. Either topical lotion or cream treatment or systemic treatment by inclusion in animal chow was satisfactory. The daily dosage for animals was 20 mg per kilogram animal chow or 10 to 15 mg applied topically.

Commerically important fur bearing animals were also used for experimentation. Two male minks were closely clipped over the back hind quarters. The animals were treated on one hind quarter and the other was used as the control. The microcapillary method for measuring hair growth was used for these studies. The animals were treated by two different methods. The animals were either fed the retinoid in their chow or they were administered the retinoid topically. The daily dose was 20 mg per kg animal chow or 5 mg per day applied topically. The results of these experiments showed that the rate of growth of new pelt was increased approximately 30% by the retinoid treatment.

Experiments using birds (canaries and parakeets) showed that inclusion of the all-trans retinoic acid or the ethyl ester of all-trans retinoic acid in bird food at a dosage of 30 mg per kilogram bird seed retarded the molting process.

The present invention may be embodied in other specific forms without departing from the spirit or the essential attributes thereof and, accordingly, reference should be made to the appended claims, rather than to the foregoing specification as indicating the scope of the invention.

I claim:

1. A method for treating alopecias caused by a shortening of the anagen (growing) phase of the hair cycle, which comprises topically applying to the scalp a retinoid in an amount which is effective to increase the rate of hair growth.

2. A method according to claim 1 wherein said retinoid is Vitamin A acid.

3. A method according to claim 1 wherein said retinoid is applied in combination with a pharmaceutically acceptable vehicle.

4. A method according to claim 3 wherein said vehicle comprises a mixture of ethanol and propylene glycol.

5. A method according to claim 4 wherein said retinoid is all-trans retinoic acid.

6. A method according to claim 1 wherein said retinoid is a compound of the formula:

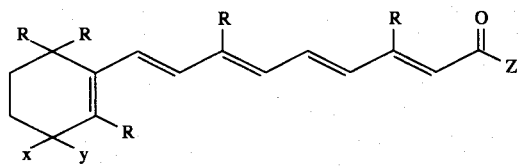

wherein R is hydrogen or a lower alkyl group, X is individually hydrogen and Y is individually hydrogen or a hydroxy group, or X and Y together form oxo, and Z is alkoxy, amine, or aklylamine, the dehydro, dihydro, anhydro and stereoisomeric forms thereof, and pharmaceutically accepted salts thereof.

7. A method according to claim 1 wherein said retinoid is selected from the group consisting of all-trans retinoic acid, all-trans retinaldehyde, all-trans retinoyl acetate, and pharmaceutically acceptable salts, ethers, amides or esters thereof.

8. A method according to claim 1 wherein said retinoid is an isomer of Vitamin A acid selected from the group consisting of 13-cis; 9,13-dicis; 9-cis; 11-cis; or 7,8-dehydro retinoic acid; Vitamin $A_2$ acid; α-Vitamin A acid; α-Vitamin A acid; 5,6-epoxy Vitamin A acid; dehydrovitamin A acid; anhydro Vitamin A acid; and pharmaceutically acceptable salts of said isomer.

9. A method according to claim 1 wherein said retinoid is used in admixture with Vitamin $D_3$ or a Vitamin $D_3$ derivative selected from the group consisting of 1-hydroxycholecalciferol; 1,25-dihydroxycholecalciferol; and 1,24-dihydroxycholecalciferol.

10. A method according to claim 1 wherein said retinoid is used in admixture with a hormone selected from the group consisting of estrogens and progesterones.

11. A method according to claim 1 wherein said retinoid is used in admixture with an antiandrogen selected from the group consisting of cyproterone acetate, spironolactone, secosteroids, flutamides, cyoctol, and decahydro-7H-benz(E)-inden-7-ones.

12. A method according to claim 1 wherein said retinoid is used in admixture with a peripheral circulatory system vasodilator which increases the blood supply to the microvasculature around the hair follicles of the scalp.

13. A method according to claim 1 wherein said retinoid comprises 0.001 to 2 percent by weight of all-trans retinoic acid in a pharmaceutically-acceptable vehicle for topical application.

14. A method for treating alopecia caused by a shortening of the anagen phase of the hair cycle which comprises topically applying to the scalp all-trans retinoic acid in an amount which is effective to increase the rate of hair growth.

15. A method for treating alopecias caused by a shortening of the anagen (growing) phase of the hair cycle, which comprises topically applying to the scalp a retinoid in an amount which is effective to stimulate hair follicles of said scalp to produce hair growth therefrom.

16. A method for treating alopecias caused by a shortening of the anagen (growing) phase of the hair cycle, which comprises topically applying to the scalp a retinoid in an amount which is effective to prolong the anagen phase of the hair cycle.

17. A method for treating alopecias caused by a shortening of the anagen (growing) phase of the hair cycle, which comprises topically applying to the scalp a retinoid in an amount which is effective to convert vellus hair to growth as terminal hair.

18. A method of increasing the rate of hair growth on mammalian skins which comprises topical or oral administration to the mammal of a retinoid in an amount which is effective to increase the rate of hair growth.

19. A method according to claim 18 wherein said mammalian skin is human scalp.

20. A method according to claim 18 wherein said retinoid is all-trans retinoic acid.

21. A method of retarding shedding in fur bearing animals comprising topical or oral administration to the animal of an effective amount of a retinoid.

22. A method according to claim 21 wherein said retinoid is all-trans retinoic acid.

23. A method of retarding molting in birds comprising topical or oral administration to the bird of an effective amount of a retinoid.

24. A method according to claim 23 wherein said retinoid is all-trans retinoic acid.

25. A composition for treating alopecias caused by a shortening of the anagen (growing) phase of the hair cycle, which comprises a retinoid in admixture with Vitamin $D_3$ or a Vitamin $D_3$ derivative selected from the group consisting of 1-hydroxycholecalciferol; 1,25-dihydroxycholecalciferol; and 1,24-dihydroxycholecalciferol, said admixture being in an amount which is effective to increase the rate of hair growth.

26. A composition for treating alopecias caused by a shortening of the anagen (growing) phase of the hair cycle, which comprises a retinoid in admixture with a hormone selected from the group consisting of estrogens and progesterones, said admixture being in an amount which is effective to increase the rate of hair growth.

27. A composition for treating alopecias caused by a shortening of the anagen (growing) phase of the hair cycle, which comprises a retinoid in admixture with an antiandrogen selected from the group consisting of cyproterone acetate, spironolactone, secosteroids, flutamides, cyoctol, and decahydro- 7H-benz(E)-inden-7-ones, said admixture being in an amount which is effective to increase the rate of hair growth.

28. A composition for treating alopecias caused by a shortening of the anagen (growing) phase of the hair cycle, which comprises a retinoid in admixture with a peripheral circulatory system vasodilator which increases the blood supply to the microvasculature around the hair follicles of the scalp, said admixture being in an amount which is effective to increase the rate of hair growth.

29. A composition according to claim 25 wherein said retinoid is not Vitamin A (retinol) per se.

30. A composition according to claim 25 wherein said retinoid is all-trans retinoic acid.

31. A composition according to claim 26 wherein said retinoid is not a Vitamin A (retinol) per se.

32. A composition according to claim 26 wherein said retinoid is all-trans retinoic acid.

33. A composition according to claim 27 wherein said retinoid is not a Vitamin A (retinol) per se.

34. A composition according to claim 27 wherein said retinoid is all-trans retinoic acid.

35. A composition according to claim 28 wherein said retinoid is not a Vitamin A (retinol) per se.

36. A composition according to claim 28 wherein said retinoid is all-trans retinoic acid.

* * * * *